(12) United States Patent
Ou Yang et al.

(10) Patent No.: US 10,814,058 B2
(45) Date of Patent: Oct. 27, 2020

(54) NASAL ASPIRATION AND WASH DEVICE

(71) Applicant: AVITA CORPORATION, New Taipei (TW)

(72) Inventors: Hsing Ou Yang, New Taipei (TW); Hsuan Hao Shih, New Taipei (TW); Ta Chieh Yang, New Taipei (TW)

(73) Assignee: AVITA CORPORATION, New Taipei (TW)

( * ) Notice: Subject to any disclaimer, the term of this patent is extended or adjusted under 35 U.S.C. 154(b) by 339 days.

(21) Appl. No.: 15/854,668

(22) Filed: Dec. 26, 2017

(65) Prior Publication Data
US 2018/0177936 A1 Jun. 28, 2018

(30) Foreign Application Priority Data

Dec. 23, 2016 (TW) .............................. 105219664 U

(51) Int. Cl.
| | | |
|---|---|---|
| *A61M 3/02* | (2006.01) | |
| *A61M 1/00* | (2006.01) | |
| *A61H 35/04* | (2006.01) | |
| *A61M 11/00* | (2006.01) | |

(52) U.S. Cl.
CPC ........... *A61M 3/0283* (2013.01); *A61H 35/04* (2013.01); *A61M 1/0003* (2013.01); *A61M 1/0058* (2013.01); *A61M 1/0062* (2013.01); *A61M 3/0258* (2013.01); *A61M 11/007* (2014.02); *A61H 2201/0153* (2013.01); *A61H 2201/0157* (2013.01); *A61H 2201/1207* (2013.01);

(Continued)

(58) Field of Classification Search
CPC .. A61M 3/0283; A61M 11/00; A61M 11/006; A61M 11/007; A61M 11/008; A61M 11/02; A61H 35/04
See application file for complete search history.

(56) References Cited

U.S. PATENT DOCUMENTS 1,856,811 A 5/1932 Inaki
6,328,718 B1 * 12/2001 Chiang ............... A61M 1/0031
604/319

(Continued)

FOREIGN PATENT DOCUMENTS

CN 202289114 7/2012
EP 1180373 A2 2/2002

(Continued)

*Primary Examiner* — Justine R Yu
*Assistant Examiner* — Kelsey E Baller
(74) *Attorney, Agent, or Firm* — Raymond Y. Chan; David and Raymond Patent Firm

(57) ABSTRACT

The present disclosure illustrates a nasal aspiration and wash device which includes a shell member, a pump, a suction part and a spray part. The pump is disposed in the shell member. The suction part is disposed on the shell member and configured to flow external gas into the pump. The spray part is disposed in the shell member and configured to spray atomized liquid out. The suction part and the spray part are spaced apart from each other a distance. The nasal aspiration and wash device of the present disclosure is able to separately perform a nasal aspiration function and a nasal wash function without interfering with each other, and the user does not need to replace a functional assembly for using the two functions.

11 Claims, 2 Drawing Sheets

(52) U.S. Cl.
CPC ............... *A61M 2205/8206* (2013.01); *A61M 2210/0618* (2013.01)

(56) References Cited

U.S. PATENT DOCUMENTS

| | | | | |
|---|---|---|---|---|
| 6,520,931 | B2* | 2/2003 | Suh | A61M 1/0062 604/118 |
| 7,862,536 | B2* | 1/2011 | Chen | A61M 1/0058 604/73 |
| 2003/0145849 | A1* | 8/2003 | Drinan | A61B 5/411 128/200.14 |
| 2016/0206835 | A1* | 7/2016 | Lee | A61M 15/0028 |

FOREIGN PATENT DOCUMENTS

| | | | |
|---|---|---|---|
| EP | 1180373 | A3 | 1/2004 |
| EP | 2005981 | A2 | 12/2008 |
| EP | 2005981 | A3 | 12/2008 |
| JP | S5836563 | | 3/1983 |
| JP | 2010527636 | | 8/2010 |
| WO | WO2008058160 | A2 | 5/2008 |
| WO | WO2008058160 | A3 | 5/2008 |
| WO | WO2010126586 | A1 | 11/2010 |

\* cited by examiner

NASAL ASPIRATION AND WASH DEVICE

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present disclosure relates to a nasal aspiration and wash device, and more particularly to a nasal aspiration and wash device which is able to perform two functions of sucking nasal mucus and spraying atomized liquid without replacing a functional assembly.

Description of Related Arts

Each of conventional nasal washer and conventional nasal aspirator is able to perform single function only, that is, the user can operate the conventional nasal aspirator to only suck a patient's nasal mucus for cleaning care, or operate the conventional nasal washer to only spray water into the patient's nasal cavity for cleaning care. When the user wants to use the nasal wash function on the conventional nasal aspirator, the user must replace the nasal aspiration assembly by a nasal wash assembly, so as to implement the spray function for washing nasal cavity; similarly, when the user wants to use the nasal aspiration function on the conventional nasal washer, the user must replace the nasal wash assembly by the nasal aspiration assembly again.

In order to solve above-mentioned problem, Taiwan Patent No. 1345462 discloses a nasal aspiration and wash device. The nasal aspiration and wash device is able to perform the nasal aspiration function and nasal wash function without replacing the functional assembly. However, the nasal aspiration and wash device disclosed in Taiwan Patent No. 1345462 include a spray port and a nasal aspiration port integrated in a single port structure, and this design causes a problem that the liquid sprayed from the spray port may be sucked by the nasal aspiration port and the nasal aspiration function and nasal wash function interfere with each other.

Therefore, what is need is to develop a nasal aspiration and wash device to solve aforementioned problem.

SUMMARY OF THE PRESENT INVENTION

Therefore, it is a primary objective of the present disclosure to provide a nasal aspiration and wash device to solve aforementioned problem.

In an embodiment, the present disclosure provides a nasal aspiration and wash device which includes a shell member, a pump, a suction part and a spray part. The pump is disposed in the shell member and includes an inhalation port configured to inhale gas and an exhaust port configured to exhaust gas. The suction part is disposed on the shell member and coupled to the inhalation port, and configured to flow external gas into the pump. The spray part is disposed in the shell member and includes a liquid storage cavity for storing liquid, and an atomization unit configured to atomize liquid provided from the liquid storage cavity and spray the atomized liquid out. The suction part and the spray part are spaced apart from each other a distance.

BRIEF DESCRIPTION OF THE DRAWINGS

The structure, operating principle and effects of the present disclosure will be described in detail by way of various embodiments which are illustrated in the accompanying drawings.

DETAILED DESCRIPTION OF THE PREFERRED EMBODIMENT

Figure 1:
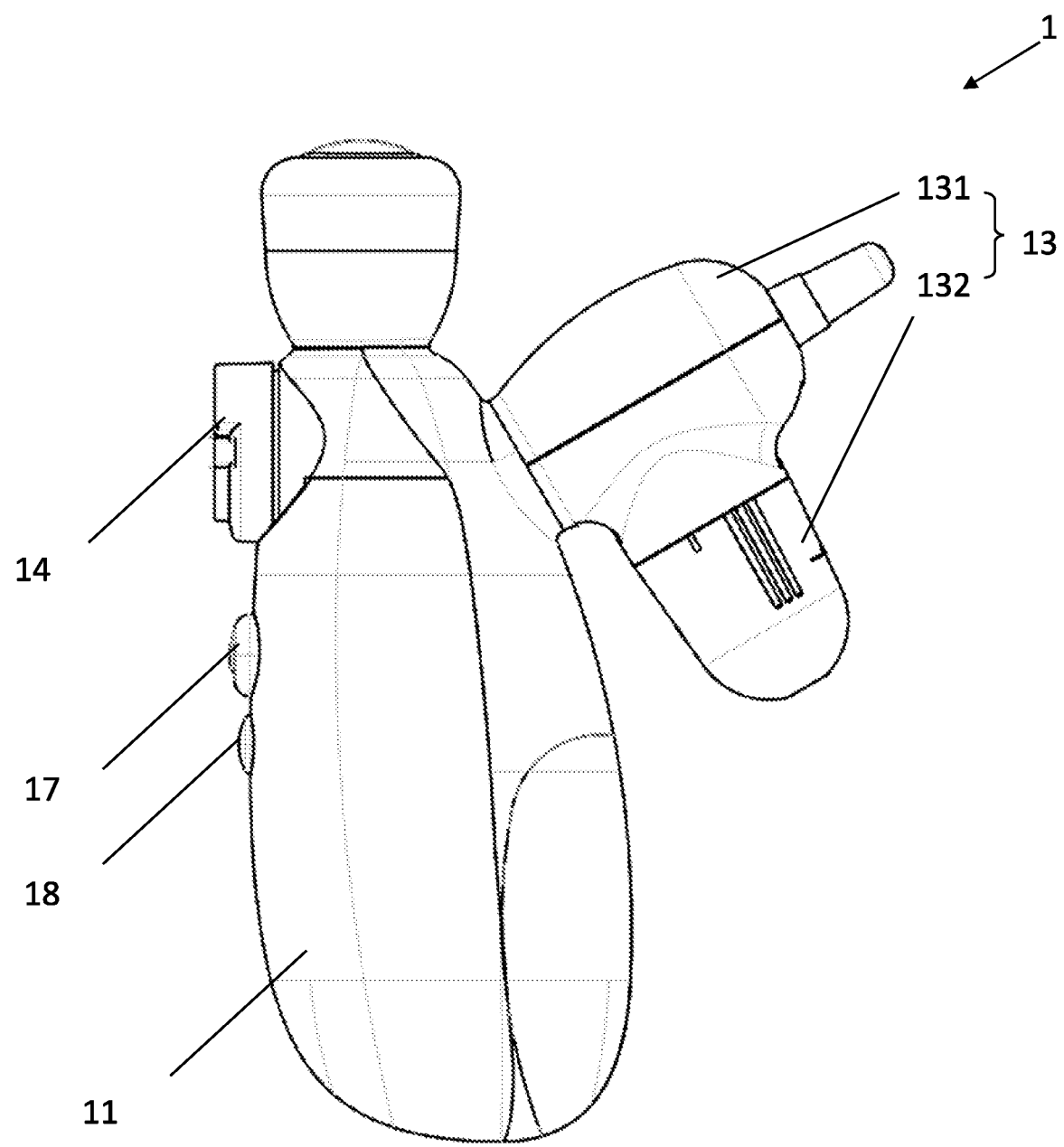
FIG. 1 is a schematic view of a nasal aspiration and wash device of the present disclosure.

The following embodiments of the present disclosure are herein described in detail with reference to the accompanying drawings. These drawings show specific examples of the embodiments of the present invention. It is to be understood that these embodiments are exemplary implementations and are not to be construed as limiting the scope of the present invention in any way. Further modifications to the disclosed embodiments, as well as other embodiments, are also included within the scope of the appended claims. These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts.

It is to be understood that, although the terms 'first', 'second', 'third', and so on, may be used herein to describe various elements, these elements should not be limited by these terms. These terms are used only for the purpose of distinguishing one component from another component. Thus, a first element discussed herein could be termed a second element without altering the description of the present disclosure. As used herein, the term "or" includes any and all combinations of one or more of the associated listed items.

Figure 2:
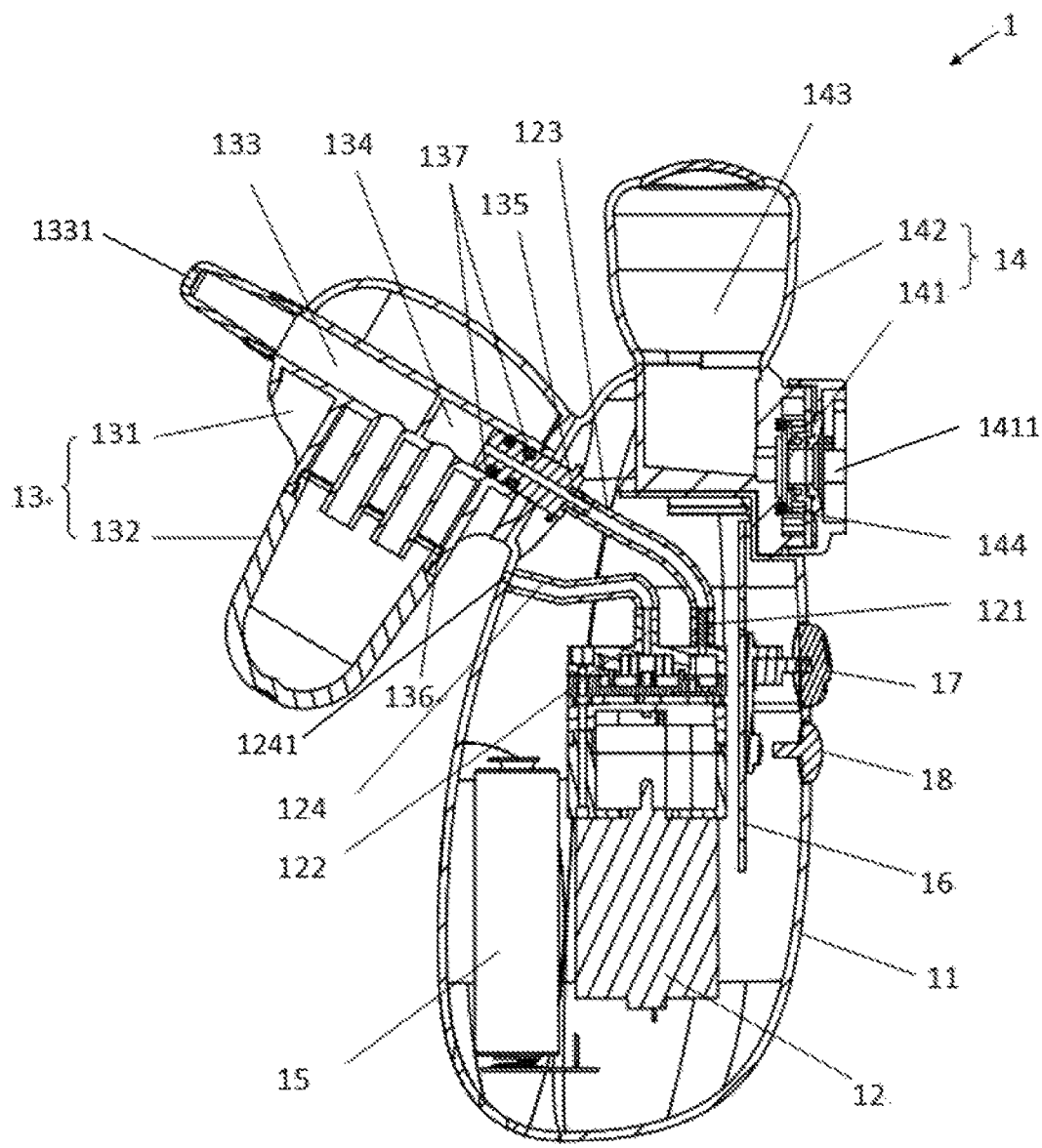
FIG. 2 is a cross-sectional schematic view of the nasal aspiration and wash device of the present disclosure.

Please refer to FIGS. 1 and 2. A nasal aspiration and wash device 1 of the present disclosure includes a shell member 11, a pump 12, a suction part 13 having a suction inlet 1331 and an exhaust outlet 1241, and a spray part 14 having a spray outlet 1411.

The shell member 11 is in a hollow handle shape. A pump 12, a battery 15 and a printed circuit board (PCB) 16 are disposed inside the shell member 11. The suction part 13 and the spray part 14 are disposed on the shell member 11. The suction inlet 1331 of the suction part 13 and the spray outlet 1411 of the spray part 14 are spaced apart from each other by a distance.

A start button 17 and an atomization button 18 are disposed on the outer surface of the shell member 11 and electrically coupled to the printed circuit board 16. The battery 15 is used to provide power to the pump 12 or the printed circuit board 16. After a user presses the start button 17, the pump 12 is activated by electronic components on the printed circuit board 16, and after the user presses the atomization button 18, the spray part 14 is activated by electronic components on the printed circuit board 16.

The pump 12 includes an inhalation port 121 and an exhaust port 122. The suction part 13 is coupled to the inhalation port 121, and a spray part 14 is coupled to the exhaust port 122. The suction inlet 1331 is communicated with the inhalation port 121 and the exhaust outlet 1241 is communicated with the exhaust port 122.

The suction part 13 includes a suction part shell 131 with the suction inlet 1331, a collection cavity 132 coupled to the suction part shell 131, and a first inhalation tube 133 and a second inhalation tube 134 disposed in the suction part shell 131. The first inhalation tube 133 has an end in communication with the collection cavity 132 and the other end in communication with external environment, for example, the other end of the first inhalation tube 133 is in communication with nasal cavity while the nasal aspiration and wash device 1 of the present disclosure is in use. The second inhalation tube 134 has an end in communication with the collection cavity 132 and the other end coupled to the inhalation port 121 through a connection tube 135. External gas can be flowed into the collection cavity 132 through the first inhalation tube 133, and then flowed into the pump 12 through the second inhalation tube 134, the connection tube 135 and an inhalation tube 123. The exhaust port 122 is coupled to hole on the shell member 11 through an exhaust tube 124, thereby exhausting the gas inhaled from the inhalation port 121.

In an embodiment, the suction part 13 may include a washer 136 disposed between the suction part shell 131 and the collection cavity 132, and an 0-shaped ring 137 disposed between the second inhalation tube 134 and the connection tube 135, thereby improving seal strength of entire tubes.

The spray part 14 includes an atomization unit 141, and a liquid storage cavity 142 for storing liquid 143 which is provided to the atomization unit 141. After the user presses the atomization button 18, the spray part 14 is activated by the electronic component on the printed circuit board 16, so that the atomization unit 141 is activated to atomize liquid 143 and spray atomized liquid out to the spray outlet 1411.

In an embodiment, the liquid 143 stored in the liquid storage cavity 142 can be medicinal liquid or water.

In another embodiment, the atomization unit 141 is an atomizer piece.

In an alternative embodiment, the spray part 14 may include an O-shaped ring 144 disposed between the atomization unit 141 and the liquid storage cavity 142 to improve seal strength.

In order to operate the nasal aspiration and wash device 1 of the present disclosure, a user can place the suction part 13 into a patient's nasal cavity, and then press the start button 17 to activate the pump 12 to inhale through the inhalation port 121, thereby sucking anomaly in the nasal cavity (such as nasal mucus) into the collection cavity 132 through the first inhalation tube 131. The sucked anomaly stays in the collection cavity 132. After the anomaly is removed from the nasal cavity, the inhaled gas is flowed into the pump 12 through the second inhalation tube 134, the connection tube 135 and the inhalation tube 123, and then exhausted through exhaust tube 124. In this embodiment, the end of the first inhalation tube 133 in communication with the collection cavity 132 and the end of the second inhalation tube 134 in communication with the collection cavity 132 are arranged side by side and toward the collection cavity 132, so that the inhaled gas can be flowed along a U-shaped path though the first inhalation tube 133, the collection cavity 132 and the second inhalation tube 134. The above content illustrates operation of the nasal aspiration function of the nasal aspiration and wash device 1 of the present disclosure.

In order to operate the spray function of the nasal aspiration and wash device 1 of the present disclosure, the user can place the spray part 14 in a patient's nasal cavity and then press the atomization button 18 to activate the atomization unit 141 of the spray part 14, so that the atomization unit 141 can atomize the liquid 143 provided from the liquid storage cavity 142 and spray the atomized liquid out to the spray outlet 1411.

In an embodiment, upon demand, the suction part 13 and the spray part 14 can be disposed on the same side surface or different side surfaces of the shell member 11, as long as the suction inlet 1331 of the suction part 13 and the spray outlet 1411 of the spray part 14 are spaced apart from each other by a distance.

In the nasal aspiration and wash device 1 of the present disclosure, the suction inlet 1331 of the suction part 13 and the spray outlet 1411 of the spray part 14 are formed in the opposite outer surface of the shell member, so that the suction inlet 1331 of the suction part 13 and the spray outlet 1411 of the spray part 14 can separately perform the nasal aspiration function and the nasal wash function without interfering with each other, and the user can use the nasal aspiration function and the nasal wash function promptly without replacing the functional assembly. Furthermore, the problem that the atomized liquid sprayed by the spray outlet 1411 of the spray part 14 may be directly sucked by the suction inlet 1331 of the suction part 13. As a result, the nasal aspiration and wash device 1 of the present disclosure has an excellent operational effect.

The present disclosure disclosed herein has been described by means of specific embodiments. However, numerous modifications, variations and enhancements can be made thereto by those skilled in the art without departing from the spirit and scope of the disclosure set forth in the claims.

What is claimed is:

1. A nasal aspiration and wash device, comprising:
   a shell member;
   a pump disposed in the shell member and comprising an inhalation port configured to inhale gas and an exhaust port configured to exhaust gas;
   a suction part having a suction inlet and an exhaust outlet formed in the shell member, wherein the suction inlet is communicated with the inhalation port, and the exhaust outlet is communicated with the exhaust port; and
   a spray part having a spray outlet formed in the shell member and a liquid storage cavity for storing liquid, and comprising an electrical atomizer configured to atomize liquid provided from the liquid storage cavity and spray the atomized liquid out to the spray outlet;
   wherein, the suction inlet of the suction part and the spray outlet of the spray part are spaced apart from each other a distance, and the exhaust outlet is provided under the suction inlet on the outer surface of the shell member.

2. The nasal aspiration and wash device according to claim 1, wherein the suction part comprises a suction part shell with the suction inlet, a collection cavity coupled to the suction part shell, and a first inhalation tube and a second inhalation tube disposed in the suction part shell, wherein the first inhalation tube comprises an end in communication with the collection cavity, and the second inhalation tube has an end in communication with the collection cavity and another end coupled to the inhalation port through a connection tube.

3. The nasal aspiration and wash device according to claim 2, wherein the end of the first inhalation tube in communication with the collection cavity and the end of the second inhalation tube in communication with the collection cavity are arranged side by side.

4. The nasal aspiration and wash device according to claim 2, wherein the suction part comprises a washer disposed between the suction part shell and the collection cavity.

5. The nasal aspiration and wash device according to claim 2, the suction part comprises an O-shaped ring disposed between the second inhalation tube and the connection tube.

6. The nasal aspiration and wash device according to claim 1, wherein the liquid stored in the liquid storage cavity is medicinal liquid or water.

7. The nasal aspiration and wash device according to claim 1, wherein the spray part comprises an O-shaped ring disposed between the electrical atomizer and the liquid storage cavity.

8. The nasal aspiration and wash device according to claim 1, wherein the suction inlet of the suction part and the spray outlet of the spray part are formed in an opposite outer surface of the shell member.

9. The nasal aspiration and wash device according to claim 1, further comprising a battery configured to provide power to the pump.

10. The nasal aspiration and wash device according to claim 1, further comprising a start button and an atomization button disposed on the outer surface of the shell member and electrically coupled to a printed circuit board to activate the suction part and the spray part.

11. The nasal aspiration and wash device according to claim 10, wherein the start button and the atomization button are disposed under the spray outlet on the outer surface of the shell member.

* * * * *